(12) United States Patent
Therin et al.

(10) Patent No.: US 7,422,596 B2
(45) Date of Patent: Sep. 9, 2008

(54) KIT COMPRISING A MEDICAL FIXING ELEMENT AND A DEVICE FOR PLACING SAID FIXING ELEMENT

(75) Inventors: Michel Therin, Lyons (FR); Francois-Regis Ory, Fontaines St Martin (FR); Pierre Bailly, Lyons (FR)

(73) Assignee: Sofradim Production, Trevoux (FR)

( * ) Notice: Subject to any disclaimer, the term of this patent is extended or adjusted under 35 U.S.C. 154(b) by 715 days.

(21) Appl. No.: 10/480,119

(22) PCT Filed: Jun. 20, 2002

(86) PCT No.: PCT/FR02/02153

§ 371 (c)(1),
(2), (4) Date: Feb. 24, 2004

(87) PCT Pub. No.: WO03/000140

PCT Pub. Date: Jan. 3, 2003

(65) Prior Publication Data

US 2004/0153102 A1 Aug. 5, 2004

(30) Foreign Application Priority Data

Jun. 21, 2001 (FR) .................................. 01 08204

(51) Int. Cl.
*A61B 17/04* (2006.01)
(52) U.S. Cl. ........................ 606/232; 606/213; 606/219; 606/224
(58) Field of Classification Search ................ 606/213, 606/216, 217, 219, 220, 221, 224, 232
See application file for complete search history.

(56) References Cited

U.S. PATENT DOCUMENTS 4,006,747 A * 2/1977 Kronenthal et al. ......... 606/144

(Continued)

FOREIGN PATENT DOCUMENTS

EP 1 090 590 A3 4/2001

(Continued)

*Primary Examiner*—Todd E. Manahan
*Assistant Examiner*—Michael G Mendoza
(74) *Attorney, Agent, or Firm*—Carter, DeLuca, Farrell & Schmidt, LLP

(57) ABSTRACT

The kit (1) comprises a needle (3) for placing the fixing element (2), and the fixing element (2) comprises at least one stop part (5) and a threaded deformable part (7) joined to said stop part (5). According to the invention, the needle (3) and the fixing element (2) comprise means (3, 10; 30) for detachably connecting the stop part (5) to the proximal part (15) of the needle (3), said connection being solid enough to enable the stop part (5) to remain integral with the needle (3) during the manipulation of the kit (1) when said kit (1) is handled, also enabling it to be introduced into the body of a patient and enabling the needle (3) to be introduced into a wall (50), said connection, however, being able to be released when a traction force is exerted upon the needle (3), in the direction in which the needle is inserted, beyond a force threshold which is greater than the stress exerted upon the fixing element (2) as a result of said manipulation, whereby release of the fixing element enables the stop part (5) to be brought into a non-deformed position by means of elastic recall of said connection.

8 Claims, 7 Drawing Sheets

U.S. PATENT DOCUMENTS

| | | |
|---|---|---|
| 4,696,300 A | 9/1987 | Anderson |
| 4,932,962 A | 6/1990 | Yoon et al. |
| 4,935,028 A | 6/1990 | Drews |
| 5,085,661 A | 2/1992 | Moss |
| 5,203,864 A | 4/1993 | Phillips |
| 5,320,633 A | 6/1994 | Allen et al. |
| 5,437,680 A | 8/1995 | Yoon |
| 6,156,044 A | 12/2000 | Kammerer et al. |
| 6,913,607 B2 * | 7/2005 | Ainsworth et al. .......... 606/151 |

FOREIGN PATENT DOCUMENTS

| | | |
|---|---|---|
| FR | 2 774 277 | 8/1999 |

* cited by examiner

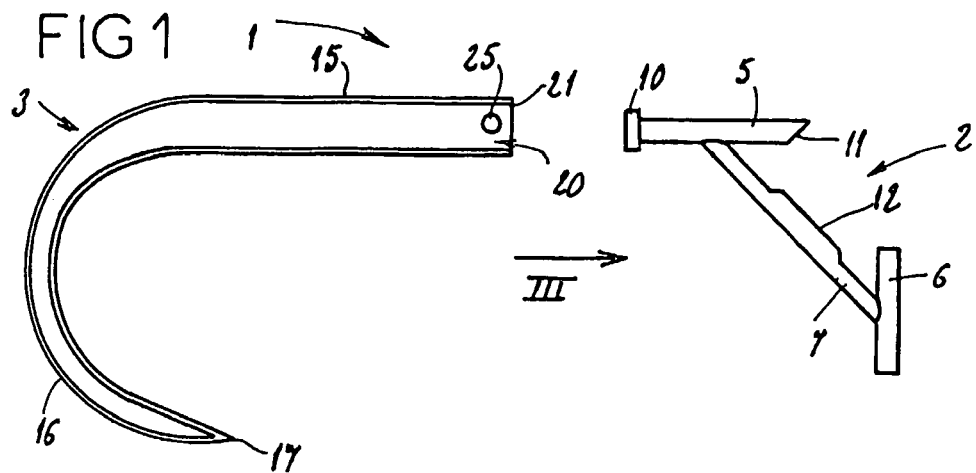
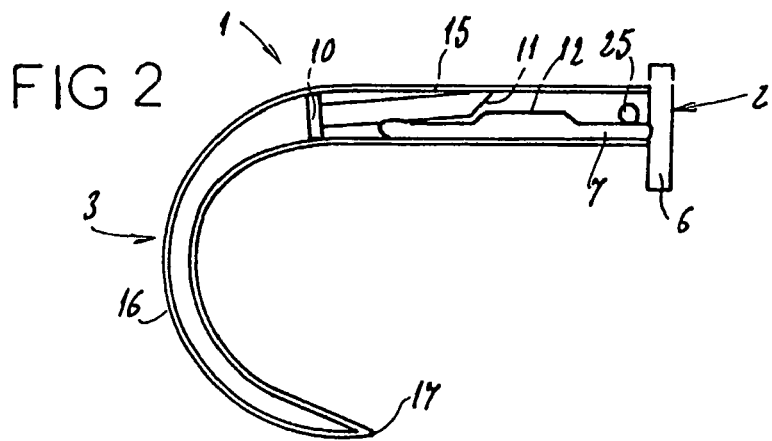
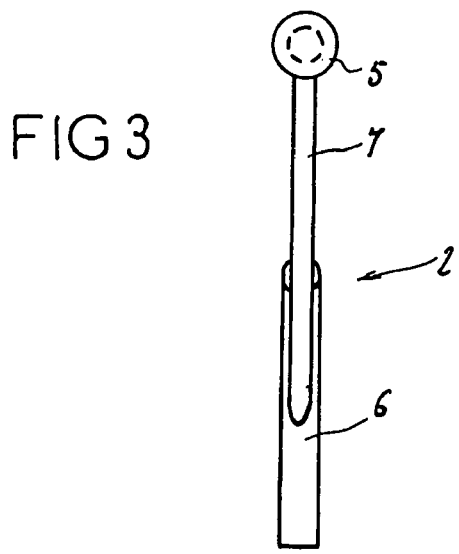

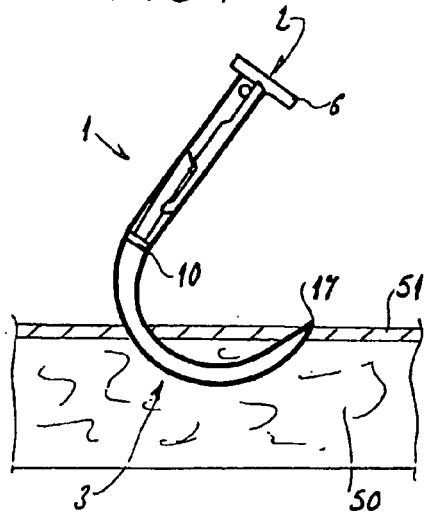
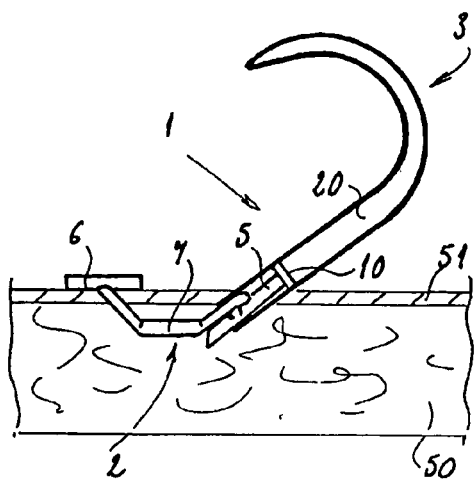
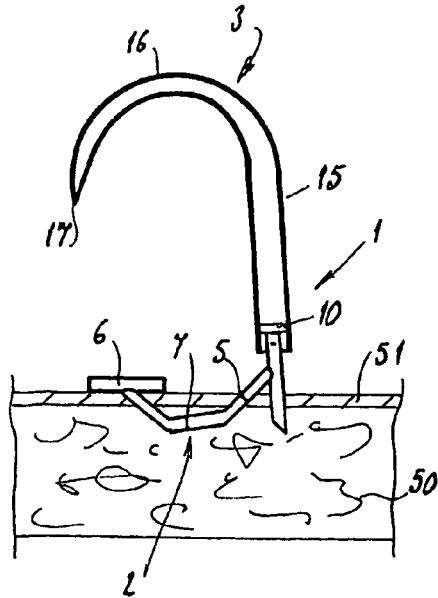
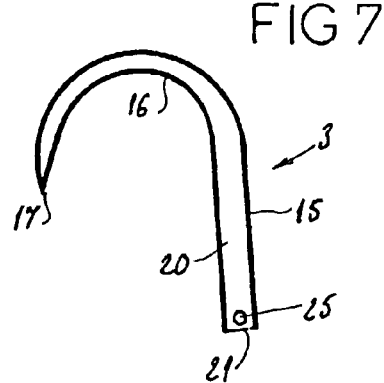
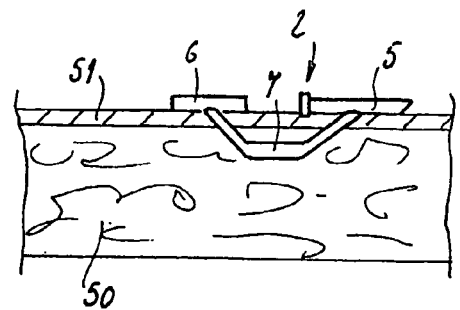

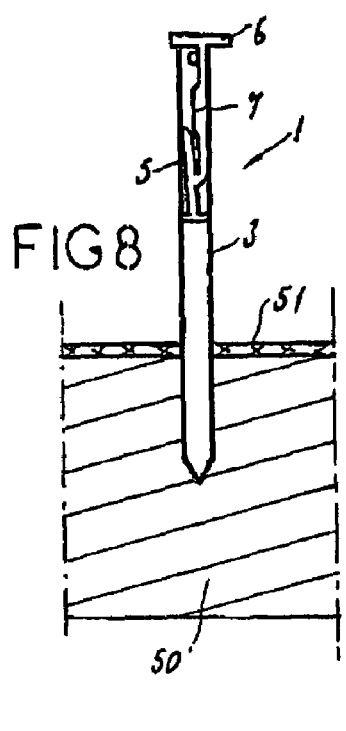
FIG 8
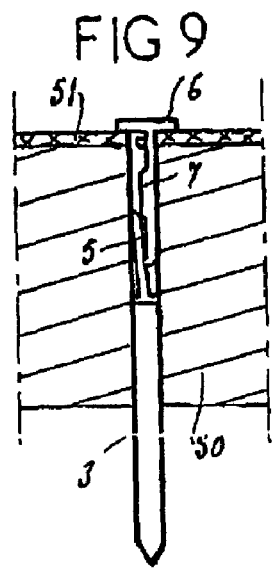
FIG 9
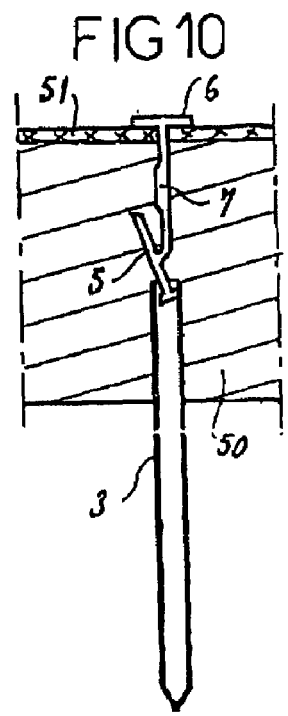
FIG 10
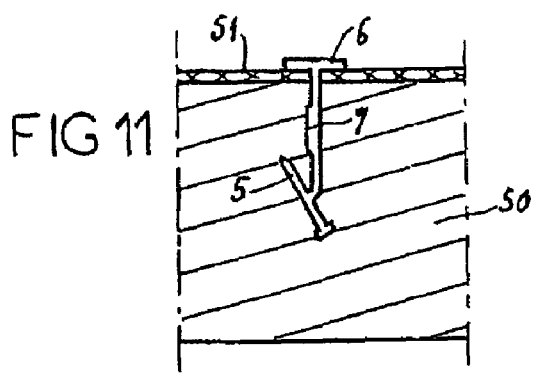
FIG 11

KIT COMPRISING A MEDICAL FIXING ELEMENT AND A DEVICE FOR PLACING SAID FIXING ELEMENT

The present invention relates to a kit comprising a medical fixing element and a needle for placing this fixing element. It also relates to a fixing element able to be used with this needle.

It is known to fix a prosthetic element or component, in particular a parietal reinforcement, to an anatomical wall, in particular to an abdominal wall, by means of at least one fixing element which is in the general shape of an H, that is to say has two stop bars joined to one another by a flexible central rod. The fixing element can pass through the wall, in which case one of the stop bars bears against the prosthetic component while the other stop bar bears against the wall on the opposite side from the prosthetic component; it is also possible for the fixing element not to pass through the wall, in which case said other stop bar is then anchored inside this wall.

Such a fixing element can also be used to join two walls of the body or two anatomical parts.

U.S. Pat. No. 5 203 864 (cf. FIG. 17), No. 5,320,633 (cf. FIG. 1D) or No. 4,696,300 (cf. FIGS. 2a, 2b) illustrate this type of fixing element and these types of fixing.

There are different types of devices available for placing these fixing elements.

A first type of device comprises a hollow needle which can be engaged through the wall or walls to be fitted and which has a distal opening. The stop bars of the fixing elements can be folded back parallel to the central rod in such a way that these fixing elements can be engaged in the cavity of the needle. The device also comprises a proximal pusher which is able to slide in the needle in order to press against the fixing element or fixing elements contained therein so as to selectively release the most distal fixing element.

A second type of device also comprises a hollow needle, but this needle is slit laterally and receives only one of the stop bars of each fixing element, the lateral slit allowing said central part and the other stop bar of each fixing element to protrude from the side of the needle.

The document U.S. Pat. No. 4,935,028 describes a surgical suturing system permitting closure of a wound or of an incision, particularly in the cornea, and including a support disk, a filiform part and a needle, the support disk being joined to one end of the filiform part and the needle being joined to the other end of this filiform part. After insertion into the cornea, the needle is separated from the filiform part or is cut, the corresponding adjacent end of this filiform part being curved to form an anchor, or receiving a stop head.

With the system according to this earlier document, the need to cut the needle from the filiform part and then to anchor or lock the end of this filiform part is something of a practical constraint, making this system incompatible with the use of minimally invasive techniques such as laparoscopy. Moreover, tensioning of the fixing element, which is necessary to ensure that the two walls to be joined are held tightly against one another, is difficult to achieve with this system. Such a hold is imperative in some cases, in particular for complete tissue integration of an abdominal wall reinforcement in the abdominal wall treated.

The document EP 1 090 590 describes a needle having a lateral slit and comprising a releasable fixing element. The system according to said document too is unable to permit the aforementioned tensioning of the fixing element.

The present invention aims to remedy the shortcomings of the prior art.

It is therefore an object of the invention to make available a kit for placing a fixing element with tension, in such a way as to ensure that the two walls to be joined are held tightly against one another.

Another object of the invention is to make available a kit particularly designed to hold an abdominal wall reinforcement pressed intimately against the abdominal wall treated, so as to ensure good tissue integration of this reinforcement to this abdominal wall.

A supplementary object of the invention is to make available a kit which is perfectly compatible with the use of minimally invasive techniques such as laparoscopy.

A further object of the invention is to make available a kit of particularly simple construction and use, so as to offer extended possibilities of application.

A further object of the invention is to make available a kit which can be disposed off after one use.

The kit in question comprises, in a manner known per se, a medical fixing element and a needle for placing this fixing element, the needle being able to be engaged through, or within the thickness of, the wall or walls intended to be fitted with the fixing element, and this fixing element having at least one stop part, able to bear against a wall, and a filiform deformable part joined to said stop part; the fixing element is elastically deformable at the area of the connection between said stop part and said filiform deformable part such that the stop part is movable relative to the filiform deformable part between a position of elastic deformation of said connection, in which the stop part and the filiform deformable part can be substantially inscribed within the cross section of the needle, and a position of nondeformation, in which the stop part is able to bear against the wall or walls and ensure anchoring of the fixing element.

According to the invention, the needle and the fixing element comprise means for detachable connection of the stop part to the proximal part of the needle, this connection being sufficiently robust to ensure that the stop part remains integral with the needle during maneuvers of the kit when taking hold of this kit, introducing it into the body of the patient, and inserting the needle into said wall, but being releasable when a traction is exerted on the needle, in the direction of insertion of the needle, beyond a force threshold greater than the stresses exerted on the fixing element by said maneuvers, the release of the fixing element making it possible to bring said stop part to the position of nondeformation, by means of elastic return of said connection.

The fixing element is thus released following a traction exerted on the needle, in the direction of insertion of this needle, which permits a certain tensioning of the fixing element with respect to the wall or walls to be fitted. This tensioning ensures that two walls to be joined are held tightly against one another, in particular an abdominal wall reinforcement and the abdominal wall treated.

The needle has a particularly simple structure and small size, making the kit in question very easy to use both with laparoscopy techniques and with direct surgical access.

The anchoring can be carried out by accessing the wall to be fitted in the area of the face of this wall intended to receive the prosthetic element, or can be carried out transcutaneously.

The simplicity of the structure of the needle also means that the kit according to the invention can be designed to be disposable, it being possible for the needle to be discarded after one use. A series of such kits could therefore be packed in a sterile package, advantageously designed to constitute, after opening, a presentation rack from which each kit can easily be removed in succession. This package can in particular be of the blister type.

This same simplicity of structure additionally means that the needle can be given all suitable shapes. In particular, the needle can have a curved or arched distal part, similar to that of suturing needles.

This curved or arched shape makes it possible in particular to carry out the fixing operation with an H-shaped fixing element as mentioned above, in which the two stop bars of the fixing element are situated on the same face of a tissue wall, in particular in the area of a parietal reinforcement, said deformable filiform part being engaged within the thickness of the wall in a curved trajectory corresponding to the trajectory of the needle in this wall during placing of the fixing element. Two stop bars are thus positioned against the prosthetic element to be implanted, in particular a parietal reinforcement, which permits reinforced and efficient anchoring of this element.

According to one possible embodiment of the invention, the needle has an inner cavity opening out in its proximal part, and it receives said stop part of the fixing element in this cavity.

Said means for detachable connection can then comprise the wall of the needle delimiting said cavity and the stop part of the fixing element; the dimensions of said cavity and of said stop part are then determined such that friction exists between this stop part and this wall of the needle.

Said means for detachable connection can also comprise, in addition to or alternatively to the friction connection cited above, one or more bosses projecting inside the cavity and able to form a "hard point" which has to be passed by said stop part in order to permit release of the fixing element.

Each boss can in particular be formed by a stamped-in part in the proximal end zone of the needle.

According to one embodiment of the invention in this case,
the needle has a proximal cavity having a constant diameter along a proximal portion intended to receive the fixing element and having a progressive reduction of this diameter along a distal portion;
the fixing element comprises a distal bar, a proximal bar and an intermediate part joining these bars to one another; the distal bar has a flange whose diameter is slightly smaller than the diameter of said proximal portion of the cavity, so that this flange can be introduced into and can slide in this proximal portion as far as the distal portion of this cavity in which this flange becomes wedged; the length of the intermediate part is such that the proximal bar comes into contact with the proximal end of the needle when the flange is in a position producing sufficient wedging of this flange.

The proximal bar coming into abutment against the proximal end of the needle thus makes it possible to define a specific degree of insertion of the flange in the cavity of the needle, corresponding to the ideal wedging to be obtained. This ideal wedging is sufficient to resist the aforementioned friction to which the fixing element is exposed, but is insufficient to risk causing damage to the fixing element when it is desired to cancel the connection between the needle and the fixing element.

According to another possible embodiment of the invention, the kit comprises a flexible filiform part joined to the proximal end of the needle and to a sleeve receiving said stop part of the fixing element.

The flexible filiform part thus increases the possibilities of mobility of the needle relative to the fixing element, which makes it easier to maneuver the needle with a view to inserting it through the wall or walls to be fitted, and permits use of a conventional suturing needle. This same flexible filiform part ensures that the fixing element is situated at a distance from the needle during maneuvering of this needle, so as to eliminate any risk of premature separation of the fixing element and needle during these maneuvers.

A simple way of obtaining the kit according to the invention in this case is to use a tube made of heat-shrinkable material, in particular polytetrafluoro-ethylene (PTFE), and to heat-shrink this material along the greater part of this tube in order to form said flexible filiform part, without heat-shrinking the rest of this tube intended to form said sleeve.

In this embodiment of the invention, said means for detachable connection can comprise the respective dimensions of the sleeve and of the fixing element, these dimensions being such that friction exists between the fixing element and the sleeve when this fixing element is inserted into this sleeve. These dimensions can in particular derive from the judicious choice of the diameter of the tube made of heat-shrinkable material.

These same means for detachable connection can comprise a lateral opening which is formed in the sleeve and in which a portion of the fixing element is engaged detachably, in particular an end of said stop part. The separation of the fixing element and of the sleeve can then be achieved by tearing the wall of the sleeve starting from this slot.

Said means for detachable connection can also comprise a thread present in the sleeve and engaged detachably around a part of the fixing element. This thread can in particular form a loop around a part of the fixing element and is breakable. In the aforementioned case of using a tube made of heat-shrinkable material, this thread is simply engaged in the tube before heat-shrinking is carried out.

According to another possible embodiment of the invention, the needle and said stop part of the fixing element are connected to one another by a material bridge dimensioned so as to rupture beyond said force threshold. In this case, the needle and the fixing element can be molded in one and the same piece of an appropriate material.

Said stop part of the fixing element can be in the form of a bar joined to said deformable filiform part approximately at its central zone.

The fixing element can comprise a single stop part or can comprise two stop parts joined to one another by said deformable filiform part.

These two stop parts permit the reinforced and efficient anchoring mentioned above.

The two stop parts can in particular be in the form of bars. The proximal stop part, given that it is not to be introduced into the needle, can have any suitable shape differing from a bar shape and capable of improving its ability to form a stop. For example, it can be in the shape of a ball, disk or ring.

Moreover, by virtue of the invention, there are no limitations to the length it is possible to give to said deformable filiform part; this deformable filiform part can in particular be formed by a thread that can be used to make a suture, the stop parts then being used to form knots; it can also have a length which is such that several successive passes of the needle through the wall or walls to be fitted are possible. In this second case, the deformable filiform part can have a relative rigidity which, when it is inserted in a curved or undulating trajectory into the wall or walls, gives it a capacity for elastic return to its rectilinear shape. This return capacity ensures that a prosthetic component is held pressed against the wall which has received the fixing element. Alternatively, for the same purpose, the deformable filiform part can have a longitudinal elasticity.

The fixing element can additionally be made of a bioabsorbable material.

To ensure that the invention is clearly understood, it is again described below with reference to the attached diagrammatic drawing which shows, by way of nonlimiting examples, several possible embodiments of the kit according to the invention and various possible embodiments of the fixing element which this kit includes.

FIG. 1 is a side view, before assembly, of the needle and of the fixing element included in this kit, according to a first embodiment;

FIG. 2 is a similar view to FIG. 1, after assembly;

FIG. 3 is a view of the fixing element according to arrow III in FIG. 1;

FIGS. 4 through 7 are side views of said kit and of a tissue wall in which the fixing element is intended to be placed, showing, respectively, four successive steps involved in placing this fixing element in this wall;

FIGS. 8 through 11 are side views of said kit in an alternative embodiment and of a tissue wall in which the fixing element is intended to be placed, showing respectively four successive steps involved in placing this fixing element in this wall;

For simplification, the parts or elements of the first embodiment which are found again in the other embodiments or variants will be designated by the same reference numbers and will not be described anew.

Figure 12:
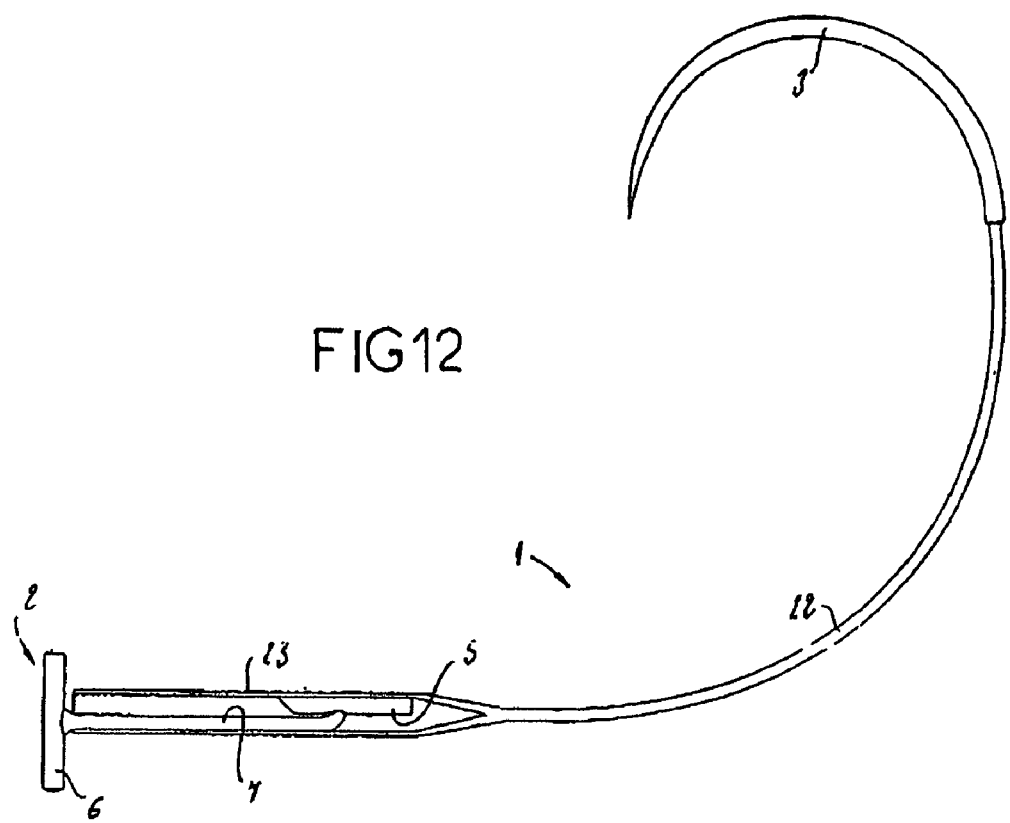
FIG. 12 is a view is a view of said kit, similar to FIG. 2, according to another embodiment of the fixing element.

FIGS. 1 and 2 show a kit 1 comprising a medical fixing element 2 and a needle 3 for placing this fixing element 2.

The fixing element 2 is molded in one piece from a deformable synthetic material which may be bioabsorbable. It comprises a first stop bar 5, a second stop bar 6, and a filiform intermediate part 7 joining these bars 5, 6 to one another.

The fixing element 2 is shown in FIG. 1 in its neutral form, that is to say in the absence of any deformation. In this shape, the bars 5, 6 form an angle of approximately 90 degrees between them, and the intermediate part 7 is oriented with respect to the bars 5, 6 substantially perpendicular to the bisecting line of the angle formed by these bars 5, 6.

Referring to FIG. 2, it will be seen that the deformability of the intermediate part 7 allows the bar 5 to be folded back in the continuation of this intermediate part 7; referring to FIG. 7, it will be seen that this same deformability allows the bars 5, 6 to be positioned substantially in the same plane after the fixing element 2 has been placed on the tissue wall 50.

The bar 5 has a diameter greater than that of the intermediate part 7, thus giving it a longitudinal rigidity greater than that of this part 7, and it is joined to the latter in the area of its central portion. At a distal end (considered with reference to the direction of engagement of the needle in the wall 50), it comprises a transverse flange 10 of a defined diameter which will be explained below. At its proximal end, it has a bevel 11. As is shown in FIG. 2, this bevel 11 forms a clearance allowing the bar 5 to be folded back against the part 7 notwithstanding a central bulge 12 which this part 7 possesses.

The bar 6 also has a diameter greater than that of the intermediate part 7, so as to have a longitudinal rigidity greater than that of this part 7, and it is also joined to the latter at its central portion. It has a purely cylindrical shape.

In addition to its aforementioned deformability, orientation and bulge 12, the intermediate part 7 has a defined length which will be explained below.

The needle 3 is made of stainless steel. It has a rectilinear proximal part 15 of tubular structure and an arched distal part 16. The diameter of the needle 3 progressively decreases in the direction toward the distal end 17 of this needle, this decrease in diameter starting at the distal end of the proximal part 15.

The proximal part 15 thus defines a cavity 20 which has a constant diameter along a wide proximal portion and has a progressive decrease in this diameter along a distal portion. As is shown in FIG. 2, the proximal portion of the cavity 20 is able to receive the bar 5 and the intermediate part 7 when this bar 5 is folded back in the continuation of this intermediate part 7; the diameter of the flange 10 is slightly smaller than the diameter of the proximal portion of the cavity 20, so that this flange 10 can be introduced into and slide in said proximal portion of this cavity 20 as far as the distal portion of this cavity 20, in which this flange 10 becomes wedged.

As is also shown in FIG. 2, the length of the intermediate part 7 is such that the bar 6 comes into contact with the proximal end 21 of the needle 3 when the flange 10 is in a position producing sufficient wedging of this flange 10 in the cavity 20. This sufficient wedging is such that it produces a detachable connection of the fixing element 2 to the proximal part 15 of the needle 3. This connection is sufficiently robust to ensure that the fixing element 2 remains secured to the needle 3 during maneuvers of the kit 1 when taking hold of said kit 1, introducing it into the patient's body and inserting the needle 3 into the wall 50 to be fitted, but is releasable when the fixing element 2 bears against the wall 50 and a manual traction is exerted by the practitioner on the needle 3.

The needle 3 additionally has, in its proximal end portion, a boss 25 projecting into the inside of the cavity 20 and formed by a stamped-in part in the wall of the needle 3. This boss 25 is able to constitute a "hard point" which has to be passed by the flange 10 in order to permit separation of the fixing element 2 from the needle 3.

In practice, and as is shown in FIGS. 4 through 7, a parietal reinforcement 51 is placed along the wall 50 to be reinforced, and the kit 1 is then brought near to this wall 50.

The arched portion 16 of the needle 3 is then inserted partially through the reinforcement 51 and the wall 50 (FIG. 4) in a circular movement centered substantially on the center generating this arched part 16, in accordance with the traditional use of a curved suturing needle.

The distal portion of the arched part 16 emerging from the wall 50 and reinforcement 51 following this insertion is then gripped and pulled until the proximal part 15 of the needle engages in the wall 50 (FIG. 5). This engagement brings the bar 6 to bear against the reinforcement 51 and causes it to unwedge the flange 10, thereby allowing the intermediate part 7 to leave the cavity 20 as the part 15 slides in the wall 50.

The needle 3 is then gradually extracted from the wall 50 and reinforcement 51 by traction exerted on it in a direction parallel to that occupied by the part 15 in FIG. 5, until complete extraction (FIG. 6). The flange 10 then comes up against the boss 25.

A traction is then exerted on the needle 3 in a direction parallel to that occupied by the part 15 in FIG. 6, to allow the flange 10 to move past the boss 25. This traction allows the bar 5 to be extracted from the cavity 20 by moving it away from the reinforcement 51, so that this bar 5 then comes to lie, through elastic return of the intermediate part 7, against the reinforcement 51 and presses this reinforcement 51 against the wall 50 (FIG. 7). The needle 3 is then removed and discarded.

The operations described above are repeated as many times as is necessary in different locations of the reinforcement 51 to ensure that this reinforcement 51 is fixed completely to the wall 50. A new kit 1 is used for each placement of a fixing element 2.

FIGS. 8 through 11 show a kit 1 very similar to that described above, except that the needle 3 is rectilinear and is engaged through the reinforcement 51 and the wall 50, the bar 5 being anchored inside this wall 50 once it is separated from the needle 3.

Figure 13:
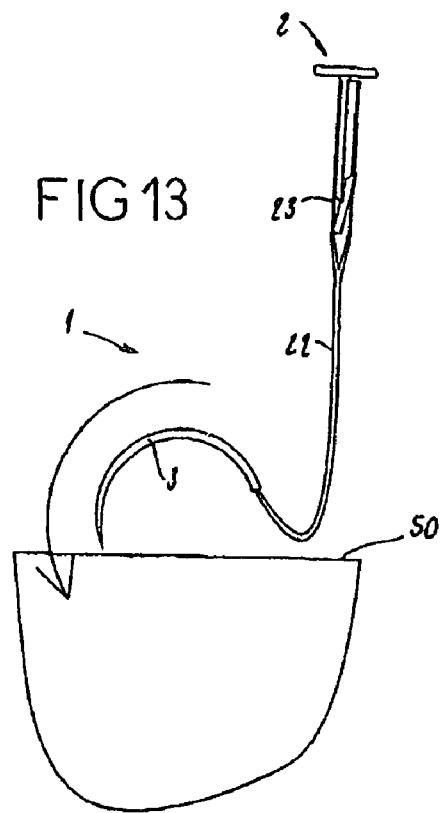
FIGS. 13 through 15 are side views of said kit and of a tissue wall in which the fixing element is intended to be placed, showing three successive steps involved in placing this fixing element in this wall.
Figure 14:
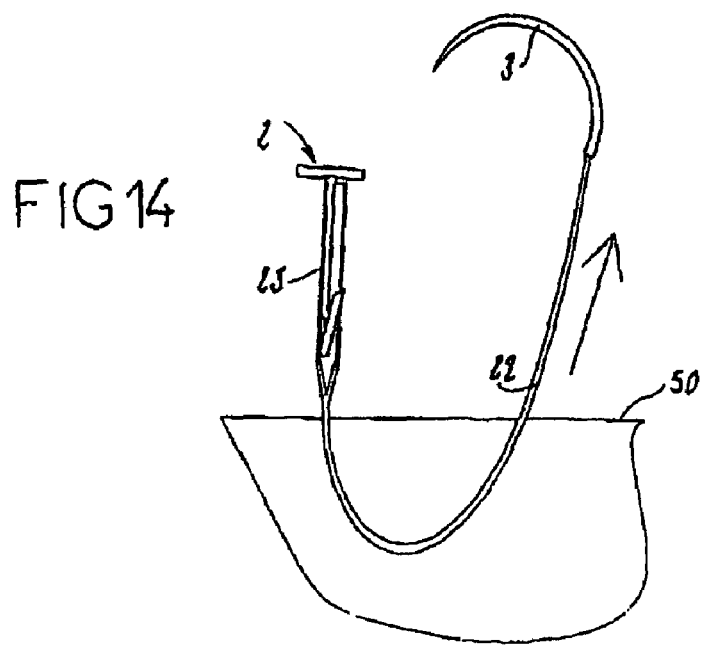

FIGS. 12 through 14 show alternative embodiments of the fixing element 2 and a second embodiment of the kit 1. The elements already described, which are found again in an identical or similar manner in these figures, are designated by the same reference numbers.

FIG. 12 shows a kit 1 in which the needle 3 is a conventional suturing needle, that is to say comprising a proximal end able to be crimped on a suture thread.

In this case, the kit 1 comprises a flexible filiform part 22, one end of which is joined to the proximal end of the needle 3 by crimping, and the other end of which is connected to a sleeve 23 receiving the stop bar 5 and the filiform part 7 of the fixing element 2.

The part 22 and the sleeve 23 are made from a tube of heat-shrinkable material, in particular polytetra-fluoroethylene (PTFE), heat-shrinking of this material being carried out on that part of said tube intended to constitute the part 22. The detachable connection between the sleeve 23 and the fixing element 2 is obtained by judicious choice of the diameter of the tube of heat-shrinkable material, this diameter being such that friction exists between the fixing element 2 and the sleeve 23 when this fixing element is inserted into this sleeve.

Figure 15:
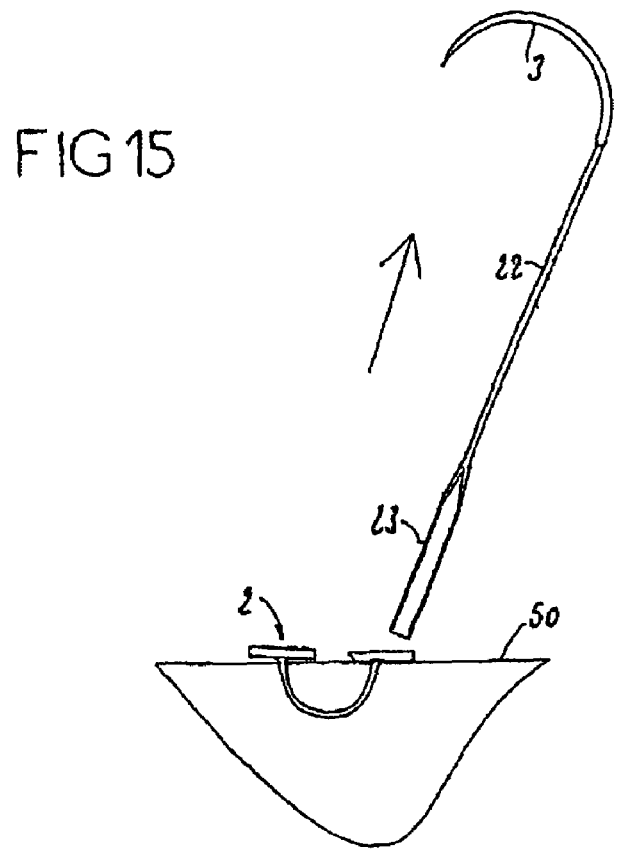

As is shown in FIGS. 13 through 15, the part 22 increases the possibilities of mobility of the needle 3 relative to the fixing element 2, making maneuvering of the needle easier. This part 22 also allows the fixing element 2 to be situated at a distance from the needle 3 during maneuvering of this needle, so as to eliminate any risk of premature separation of the fixing element 2 and needle 3 during these maneuvers.

Figure 16:
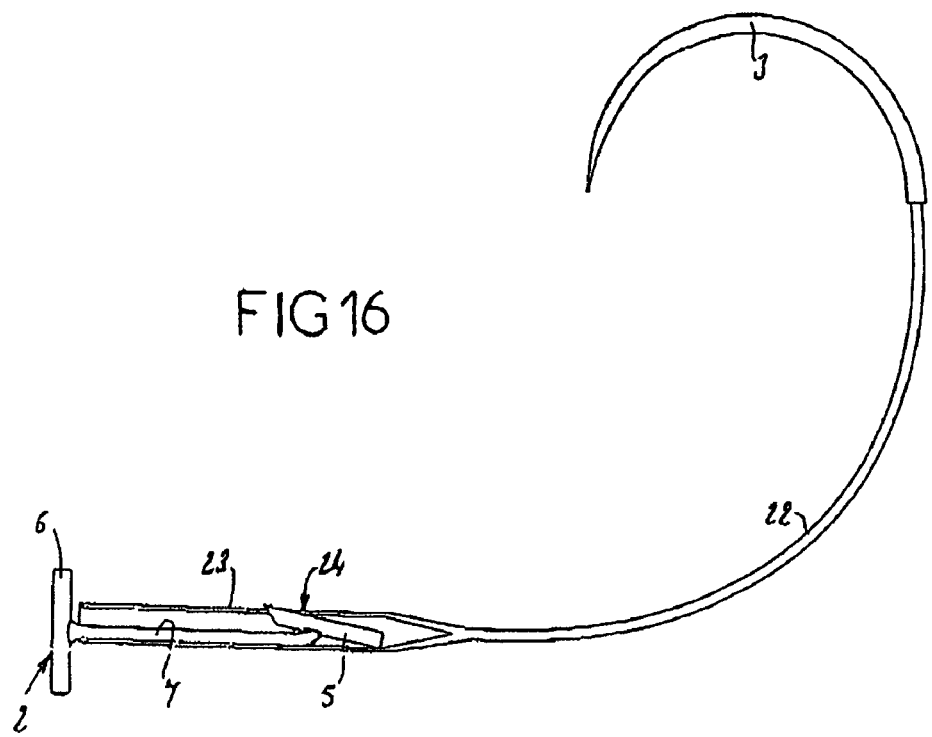
FIG. 16 is a view is a view of said kit, similar to FIG. 12, according to an alternative embodiment.

In the case of the kit 1 shown in FIG. 16, a lateral opening 24 is formed in the sleeve 23, and an end of the stop bar 5 is engaged detachably in this slot 24. The separation of the fixing element 2 and sleeve 23 can then be obtained by partial or complete tearing of the wall of the sleeve starting from this slot 24.

Figure 17:
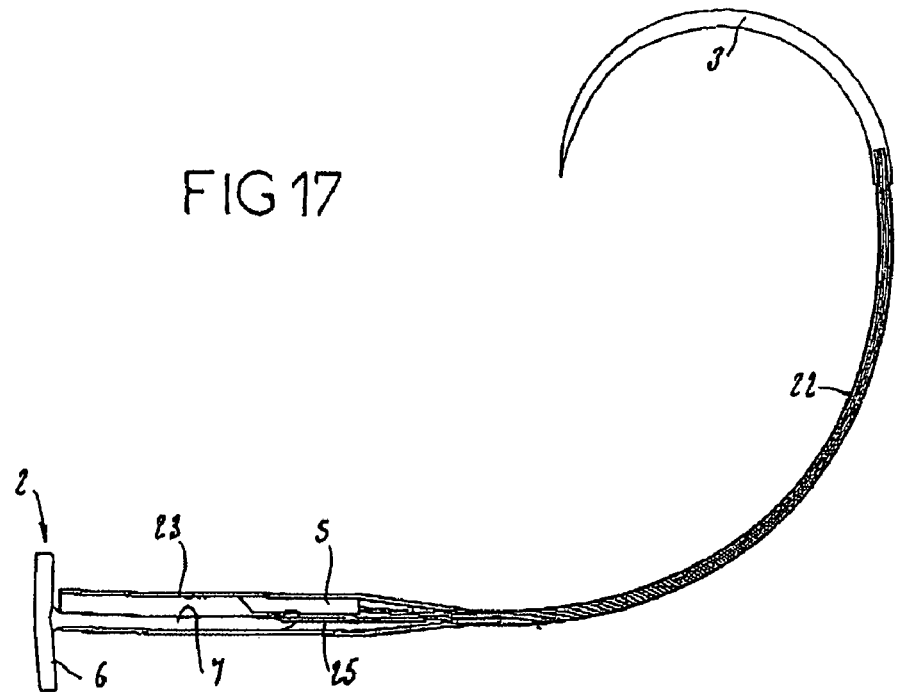
FIG. 17 is a view is a view of said kit, similar to FIG. 12, according to another embodiment.

The kit 1 shown in FIG. 17 also comprises a part 22 and a sleeve 23 formed by a tube of heat-shrinkable material. In this case, a breakable thread 25 forming a loop around the bar 5 is engaged in the tube before heat-shrinking. This thread 25 permits the detachable connection between the sleeve 23 and the fixing element 2.

Figure 18:
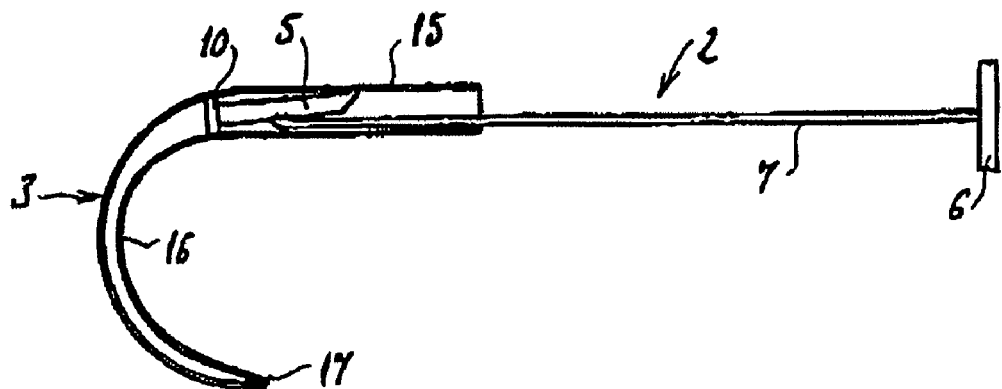
FIG. 18 is a view of said kit, similar to FIG. 2, according to an alternative embodiment of the fixing element.

In the case of FIG. 18, the intermediate part 7 has a length such that several successive passes of the needle 3 through the wall 50 are possible.

Figure 19:
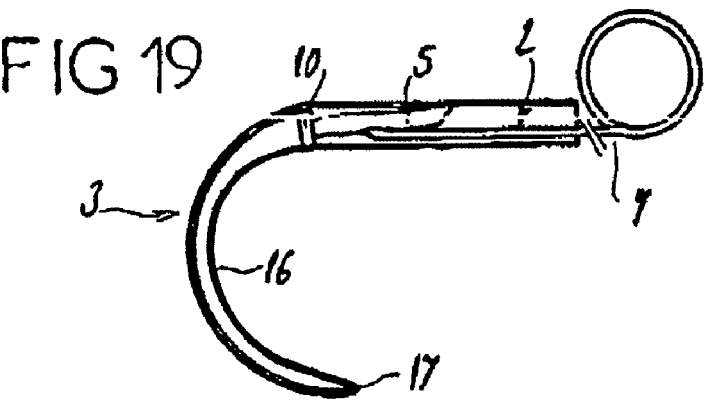
FIG. 19 is a view of said kit, similar to FIG. 2, in another alternative embodiment of the fixing element.

In the case of FIG. 19, the intermediate part 7 is formed by a thread which can be used to form a suture.

This thread is wound on a bobbin the time of introduction of the kit 1 into the patient's body.

Figure 20:
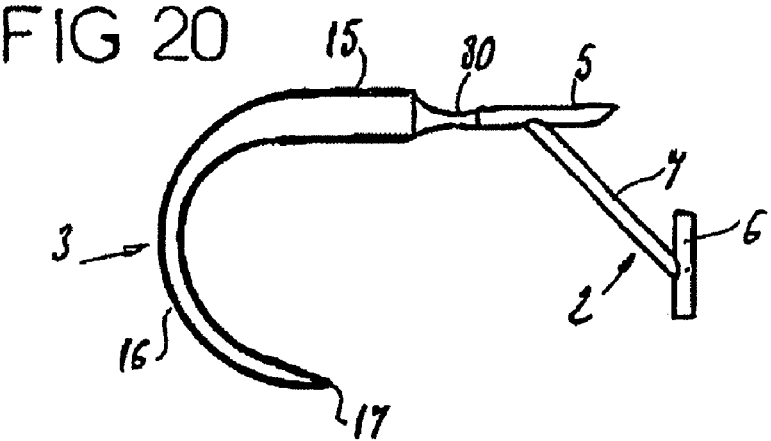
FIG. 20 is a view of said kit, similar to FIG. 2, in another embodiment.

In the case of FIG. 20, the needle 3 and the fixing element 2 are molded in one and the same piece of material. The needle 3 and the bar 5 are then joined to one another by a material bridge 30 dimensioned so as to rupture beyond the aforementioned force threshold.

As will be evident from the foregoing, the invention provides a kit 1 which has numerous advantages compared to similar systems in the prior art. The decisive advantage of this kit 1 lies in its simple structure and straightforward function and the fact that it offers extended possibilities of use. In particular, this kit is very easy to use both with laparoscopy techniques and with direct access techniques; anchoring can be achieved by accessing the wall to be fitted, in the area of the face of said wall intended to receive the prosthetic element, or it can be achieved transcutaneously; the kit 1 can be designed to be discarded after one use, and makes it possible to give the distal part of the needle any suitable shape, in particular a curved or arched shape, and to use different types of fixing elements.

It goes without saying that the invention is not limited to the embodiment described above by way of example and that instead it encompasses all alternative embodiments falling within the scope of protection defined by the attached claims. Thus, the fixing element 2 can be used not only to fix a prosthetic element or component, in particular a parietal reinforcement 51, to an anatomical wall 50, in particular an abdominal wall, but also to join two anatomical walls or two anatomical parts to one another, or to fix any other type of component or element to such a wall; a straight needle can be used to engage the fixing element through a fold formed in a tissue; the means for detachable connection of the fixing element 2 can comprise a slit formed in the proximal end of the needle, giving the needle a flexibility allowing it to retain the fixing element; the curved needle can be of the "three eighths" type, that is to say having a shape corresponding substantially to three eighths of a circle; the fixing element can extend beyond the proximal end of this needle.

The invention claimed is:

1. A kit (1) comprising a medical fixing element (2) and a needle (3) for placing the fixing element (2), the needle (3) being able to be engaged through, or within a thickness of, a wall or walls (50) intended to be fitted with the fixing element (2), and the fixing element (2) having at least one stop part (5), able to bear against the wall (50), and a filiform deformable part (7) joined to said stop part (5); the fixing element (2) is elastically deformable at an area of a connection between said stop part (5) and said filiform deformable part (7) such that the stop part (5) is movable relative to the filiform deformable part (7) between a position of elastic deformation of said connection, in which the stop part (5) and the filiform deformable part (7) can be substantially inscribed within a cross section of the needle (3), and a position of nondeformation, in which the stop part (5) is able to bear against the wall or walls (50) and ensure anchoring of the fixing element (2);

the kit (1) being characterized in that the needle (3) and the fixing element (2) comprise means (3, 10; 30) for detachable connection of the stop part (5) to a proximal part (15) of the needle (3), the connection being sufficiently robust to ensure that the stop part (5) remains integral with the needle (3) during maneuvers of the kit (1) when taking hold of the kit (1), introducing it into the body of the patient, and inserting the needle (3) into said wall (50), but being releasable when a traction is exerted on the needle (3), in the direction of insertion of the needle, beyond a force threshold greater than the stresses exerted on the fixing element (2) by said maneuvers, the release of the fixing element making it possible to bring said stop part (5) to the position of nondeformation, by means of elastic return of said connection, the needle (3) has a proximal cavity (20) having a constant diameter along a proximal portion intended to receive the fixing element (2) and having a progressive reduction of the diameter along a distal portion; the fixing element (2) comprises a distal bar (5), a proximal bar (6) and an intermediate part (7) joining these bars (5, 6) to one another; the distal bar (5) has a flange (10) whose diameter is slightly smaller than the diameter of said proximal portion of the cavity (20), so that the flange (10) can be introduced into and can slide in the proximal portion as far as the distal portion of the cavity (20) in which the flange (10) becomes wedged; the length of the intermediate part (7) is such that the proximal bar (6) comes into contact with the proximal end (21) of the needle (3) when the flange (10) is in a position producing sufficient wedging of the flange (10).

2. The kit (1) as claimed in claim 1, characterized in that the needle (3) and the stop part (5) of the fixing element (2) are joined to one another by a material bridge (30) dimensioned so as to rupture beyond said force threshold.

3. The kit (1) as claimed in claim 2, characterized in that the needle (3) and the fixing element (2) are molded in one and the same piece of material.

4. The kit (1) as claimed in claim 1, characterized in that said means for detachable connection comprise:
respective dimensions of the sleeve (23) and of the fixing element (2), these dimensions being such that friction exists between the fixing element (2) and the sleeve (23) when the fixing element (2) is inserted into the sleeve (23); and/or
a lateral opening (24) which is formed in the sleeve (23) and in which a portion of the fixing element (2) is engaged detachably, in particular an end of said stop part (5); and/or
a thread (25) present in the sleeve (23) and engaged detachably around a part (5, 7) of the fixing element (2).

5. The kit (1) as claimed in claim 4, characterized in that the thread (25) forms a loop around a part (5, 7) of the fixing element (2) and is breakable.

6. A kit (1) comprising a needle (3); and a fixing element (2) having at least one stop part (5), able to bear against a wall (50), and a filiform deformable part (7) joined to said stop part (5), the fixing element (2) being elastically deformable at the area of the connection between said stop part (5) and said filiform deformable part (7) such that the stop part (5) is movable, relative to the filiform deformable part (7), between a position of elastic deformation of said connection, in which the stop part (5) and the filiform deformable part (7) can be substantially inscribed within a cross section of a proximal part (15) of the needle (3), and a position of nondeformation, in which the stop part (5) is able to bear against the wall or walls (50) and ensure anchoring of the fixing element (2);
characterized in that the kit (1) includes means (10;30) for detachable connection of the stop part (5) to the proximal part (15) of the needle (3), the needle (3) having a proximal cavity (20) having a constant diameter along a proximal portion intended to receive the fixing element (2) and having a progressive reduction of the diameter along a distal portion, the connection being sufficiently robust to ensure that the stop part (5) remains integral with the needle (3) during maneuvers of the kit (1) when taking hold of the kit (1), introducing it into the body of the patient, and inserting the needle (3) into said wall (50), but being releasable when a traction is exerted on the needle (3), in the direction of insertion of the needle, beyond a force threshold greater than the stresses exerted on the fixing element (2) by said maneuvers, the stop part (5) having a flange whose diameter is slightly smaller than the diameter of the proximal portion as far as the distal portion of the cavity in which the flange becomes wedged, the release of the fixing element making it possible to bring said stop part (5) to the position of nondeformation, by means of elastic return of said connection, the deformable filiform part (7) of the fixing element (2) being formed by a thread that can be used to make a suture.

7. A kit (1) comprising a needle (3); and a fixing element (2) having at least one stop part (5), able to bear against a wall (50), and a filiform deformable part (7) joined to said stop part (5), the fixing element (2) being elastically deformable at the area of the connection between said stop part (5) and said filiform deformable part (7) such that the stop part (5) is movable, relative to the filiform deformable part (7), between a position of elastic deformation of said connection, in which the stop part (5) and the filiform deformable part (7) can be substantially inscribed within a cross section of a proximal part (15) of the needle (3), and a proximal part (15) of the needle (3), and a position of nondeformation, in which the stop part (5) is able to bear against the wall or walls (50) and ensure anchoring of the fixing element (2);
characterized in that the kit (1) includes means (10;30) for detachable connection of the stop part (5) to the proximal part (15) of the needle (3), the needle (3) having a proximal cavity (20) having a constant diameter along a proximal portion intended to receive the fixing element (2) and having a progressive reduction of the diameter along a distal portion, the connection being sufficiently robust to ensure that the stop part (5) remains integral with the needle (3) during maneuvers of the kit (1) when taking hold of the kit (1), introducing it into the body of the patient, and inserting the needle (3) into said wall (50), but being releasable when a traction is exerted on the needle (3), in the direction of insertion of the needle, beyond a force threshold greater than the stresses exerted on the fixing element (2) by said maneuvers, the stop part (5) having a flange whose diameter is slightly smaller than the diameter of the proximal portion as far as the distal portion of the cavity in which the flange becomes wedged, the release of the fixing element making it possible to bring said stop part (5) to the position of nondeformation, by means of elastic return of said connection,
the deformable filiform part (7) of the fixing element (2) having a length such that several successive passes of the needle (3) through the wall or walls (50) to be fitted are possible.

8. A fixing element (2) A kit (1) comprising a needle (3); and a fixing element (2) having at least one stop part (5), able to bear against a wall (50), and a filiform deformable part (7) joined to said stop part (5), the fixing element (2) being elastically deformable at the area of the connection between said stop part (5) and said filiform deformable part (7) such that the stop part (5) is movable, relative to the filiform deformable part (7), between a position of elastic deformation of said connection, in which the stop part (5) and the filiform deformable part (7) can be substantially inscribed within a cross section of a proximal proximal part (15) of the needle (3), and a position of nondeformation, in which the stop part (5) is able to bear against the wall or walls (50) and ensure anchoring of the fixing element (2);
characterized in that the kit (1) includes means (10;30) for detachable connection of the stop part (5) to the proximal part (15) of the needle (3), the needle (3) having a proximal cavity (20) having a constant diameter along a proximal portion intended to receive the fixing element (2) and having a progressive reduction of the diameter along a distal portion, the connection being sufficiently robust to ensure that the stop part (5) remains integral with the needle (3) during maneuvers of the kit (1) when taking hold of the kit (1), introducing it into the body of the patient, and inserting the needle (3) into said wall (50), but being releasable when a traction is exerted on the needle (3), in the direction of insertion of the needle, beyond a force threshold greater than the stresses exerted on the fixing element (2) by said maneuvers, the stop part (5) having a flange whose diameter is slightly smaller than the diameter of the proximal portion as far as the distal portion of the cavity in which the flange becomes wedged, the release of the fixing element making it possible to bring said stop part (5) to the position of nondeformation, by means of elastic return of said connection, characterized in that its filiform part (7) having a relative rigidity which, when it is inserted in a curved or undulating trajectory into the wall or walls (50) to be fitted, gives it a capacity for elastic return to its rectilinear shape.

* * * * *